United States Patent
Miller et al.

(10) Patent No.: US 6,692,941 B1
(45) Date of Patent: Feb. 17, 2004

(54) BOVINE GROWTH HORMONE

(75) Inventors: Walter L. Miller, San Francisco, CA (US); Joseph Augustin Martial, Mill Valley, CA (US); John D. Baxter, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1,826 days.

(21) Appl. No.: 07/480,745

(22) Filed: Feb. 15, 1990

Related U.S. Application Data

(63) Continuation of application No. 07/090,937, filed on Aug. 28, 1987, now abandoned, which is a continuation of application No. 06/489,557, filed on Apr. 28, 1983, now abandoned, which is a continuation of application No. 06/181,348, filed on Aug. 26, 1980, now abandoned.

(51) Int. Cl.$^7$ ............... C12N 15/00; C12N 15/18; C12P 21/02
(52) U.S. Cl. .............. 435/69.4; 435/243; 435/252.3; 536/23.51
(58) Field of Search ................ 435/69.4, 70.1, 435/71.1, 71.2, 91, 172.1, 172.3, 320, 252.5, 252.35, 320.1, 91.1, 243; 536/27; 935/13, 29, 72, 73; 530/399

(56) References Cited

U.S. PATENT DOCUMENTS

| | | | |
|---|---|---|---|
| 4,415,732 A | * 11/1983 | Caruthers et al. | ........... 536/26.5 |
| 4,458,066 A | * 7/1984 | Caruthers et al. | ........ 536/25.34 |
| 5,037,806 A | 8/1991 | Krivi | ............................ 514/12 |
| 5,221,619 A | * 6/1993 | Itakura et al. | .............. 435/69.4 |

FOREIGN PATENT DOCUMENTS

| | | |
|---|---|---|
| EP | 0 001 930 A2 | 5/1979 |
| EP | 0 001 929 A2 | 6/1979 |
| EP | 0012 494 A1 | 6/1980 |

OTHER PUBLICATIONS

Wallis et al ; FEBS Letters 35: 11 (1973).*
Goeggel et al; Nature 281: 544 (1979).*
Crea et al; Proc. Natl. Acad. Sci. USA 75: 5765 (1978).*
Caruthers et al, in *Nucleic Acids Synthesis: Applications to Molecular Biology and Genetic Engineering*, Koster (ed.), Nucleic Acids Research Symposium Series No. 7, 215 (1980).*
Santome et al., "Primary Structure of Bovine Growth Hormone", *Eur. J. Biochem.* 37:164–170 (1973).
Perter et al., "The Evolution of Genes: the Chicken Preproinsulin Gene", *Cell* 20:555–566 (1980).
Martial et al., "Human Growth Hormone: Complementary DNA Cloning and Expression in Bacteria", *Science* 205:602–607 (1979).
Seeburg et al., "Nucleotide Sequence and Amplification in Bacteria of Structural Gene for Rat Growth Hormone", *Nature* 270:486–494 (1977).
Goodman and MacDonald, "Cloning of Hormone Genes from a Mixture of cDNA Molecules", *Methods in Enzymology* 68:75–90 (1979).
Seeburg et al., "Nucleotide Sequence of Part of the Gene for Human Chorionic Somatomammotropin: Purification of DNA Complementary to Predominant mRNA Species", *Cell* 12:157–165 (1977).
Roskam et al., "Molecular Cloning and Nucleotide Sequence of the Human Growth Hormone Structural Gene", *Nucl. Acids Res.* 7:305–320 (1979).
Woychik et al., "Cloning and Nucleotide Sequencing of the Bovine Growth Hormone Gene", *Nucl. Acids Res.* 10:7197–7210 (1982).
Graf et al., "On the Primary Structure of Pituitary Bovine Browth Hormone", *Biochem. Biophys. Res. Comm.* 56:168–176 (1974).
Lomedico et al., "The Structure and Evolution of the Two Nonallelic Rat Preproinsulin Genes", *Cell* 18:545–558 (1979).
Miller et al., "Molecular Cloning of Gene Sequences Coding for Bovine Growth Hormone and Prolactin", *Pediatric Research* 14, Abstract 335 (1980).
Nilson et al., "Ontogeny of Pituitary Hormone mRNAs in the Bovine Fetus", *J. Biol. Chem.* 255:5871–5878 (1980).
Seeburg et al., "Synthesis of Growth Hormone by Bacteria", *Nature* 276:795–798 (1978).
Efstratiades et al., "Cloning of Double–Stranded cDNA", *Genetic Engineering Principles and Methods* 1:15–36 (1979).
Gilbert et al., "Useful Proteins from Recombinant Bacteria", *Scientific American* 242:74–94 (1980).
Nilson et al., "Construction and Characterization of a cDNA Clone Containing a Portion of the Bovine Prolactin Sequence", *Nucl. Acids Res.* 8:1561–1573 (1980).
Lingappa et al., "Nascent Prehormones are Intermediates in the Biosynthesis of Authentic Bovine Pituitary Growth Hormone and Prolactin", *Proc. Nat. Acad. Sci. (USA)* 74:2432–2436 (1977).
Niall et al., "The Chemistry of Growth Hormone and the Lactogenic Hormones", *Recent process in Hormone Research* 29:387–416 (1973).
Wallis et al., "Molecular Evolution of Pituitary Growth Hormone", *Biochemical Society* Transactions, 549th Meetina, Cambridge 2:911–912 (1974).
Harpold et al., "The Synthesis and Processing of a Nuclear RNA Precursor to Rat Pregrowth Hormone Messenger RNA", *Nucleic Acids Research* 6:3133–3144 (1979).
Maxam et al., "A New Method for Sequencing DNA", *Proc. Natl. Acad. Sci. (USA)* 74:560–564 (1977).

* cited by examiner

*Primary Examiner*—James Martinell
(74) *Attorney, Agent, or Firm*—Morrison & Foerster LLP

(57) ABSTRACT

A DNA comprising a deoxynucleotide sequence coding for bovine growth hormone is described. A transfer vector and an expression vector containing this DNA and microorganisms transformed by these vectors are also described.

21 Claims, 2 Drawing Sheets

FIG. 1

```
                                                          -26
                                              met met ala ala gly pro arg thr ser leu leu leu ala phe ala leu
ACGGCTCAGGGTCCGTGACGCTCACCAGCT ATG ATG GCT GCA GGC CCC CGG ACC TCC CTG CTC CTG GCT TTC GCC CTG
                                                                              -20                           -10
leu cys leu pro trp thr gln val val gly ala phe pro ala met ser leu ser gly leu phe ala asn ala
CTC TGC CTG CCC TGG ACT CAG GTG GTG GGC GCC TTC CCA GCC ATG TCC TTG TCC GGC CTG TTT GCC AAC GCT
                                                   1                                                     10
val leu arg ala gln his leu his gln leu ala ala asp thr phe lys glu phe glu arg thr tyr ile pro
GTG CTC CGG GCT CAG CAC CTG CAC CAG CTG GCT GCT GAC ACC TTC AAA GAG TTT GAG CGT TAC ATC CCG
                               20                                         30
glu gly gln arg tyr ser ile gln asn thr gln val ala phe cys phe ser glu thr ile pro ala pro thr
GAG GGA CAG AGA TAC TCC ATC CAG AAC ACC CAG GTT GCC TTC TGC TTC TCC GAA ACC ATC CCG GCC CCC ACG
           40                                                   50                                60
gly lys asn glu ala gln gln lys asp ser arg val phe thr asn ser leu val phe gly thr ile leu leu leu ile gln ser trp
GGC AAG AAT GAG GCC CAG CAG AAA TCA GAC AGA GTC TTC ACC AAC AGC TTG GTG TTT GGC ACC ATC CTG CTC CTC ATC CAG TCG TGG
           70                                          80                                         110
leu gly pro leu gln phe leu ser arg val phe gly thr ile leu leu ile gln ser trp
                                                                                                        tyr
                                                                                                        TAT
leu gly pro leu gln phe leu ser arg val phe gly thr ser asp arg val tyr
CTT GGG CCC CTG CAG TTT CTC AGC AGA GTC TTC GGC ACC TCG GAC CGT GTC
                       90                                                    100
glu lys lys asp leu glu glu gly ile leu met arg glu leu glu asp ala leu leu lys asn
GAG AAG AAG GAC CTG GAG GAA CTG ATG CGG GAG CTG GAA GAT GCC CTG CTG AAG AAC
                                                                       130
gly gln ile leu lys gln thr tyr asp lys phe asp thr asn met arg ser asp ala leu leu lys asn
GGG CAG ATC CTC AAG CAG ACC TAT GAC AAA TTT GAC ACA AAC ATG CGG AGT GAC GCG CTG CTC AAG AAC
       140                                         150
                                                              170                              180
tyr gly leu leu ser cys phe arg lys asp leu his lys thr glu thr tyr leu arg val met lys cys arg
TAC GGT CTG CTG TCC TGC TTC CGG AAG GAC CTG CAT AAG ACG GAG ACG TAC CTG AGG GTC ATG AAG TGC CGC
                      160
arg phe gly glu ala ser cys ala phe AM
CGC TTC GGG GAG GCC AGC TGT GCC TTC TAG TTGCCAGCCATCTGTTGTTTGCCCCTCCCCCGTGCCTTCCTTGACCCTGAAGG
190 191
TGCCACTCCCACTGTCCTTTCCTAATAAATGAGGAAATTGCATCGC[poly A]
```

BOVINE GROWTH HORMONE

This application is a continuation of U.S. Ser. No. 07/090,937, filed Aug. 28, 1987 now abandoned, which is a continuation of U.S. Ser. No. 06/489,557 filed Apr. 28, 1983, which is a continuation of U.S. Ser. No. 06/181,348 filed Aug. 26, 1980, all now abandoned.

BACKGROUND OF THE INVENTION

Growth hormone is a polypeptide hormone synthesized in and secreted by the adenohypophysis (anterior lobe of the pituitary). Growth hormone is synthesized as a precursor protein (pre-growth hormone) containing an N-terminal signal peptide and the growth hormone sequence. The amino acid sequence for bovine growth hormone has been determined (Dayhoff, M. D., et al, *Atlas of Protein Sequence and Structure*, Vol. 5, Supp. 3, pp. 345–352, National Biomedical Research Foundation, Washington, D.C. (1978).

Growth hormone is normally produced throughout life, although in highest amounts during the pre-adult period. The hormone is required for pre-adult growth. Although its mechanism is not understood in detail, growth hormone is known to promote skeletal growth, nitrogen retention, protein synthesis and affects glucose and lipid metabolism. In other words, growth hormone is a general anabolic agent.

Uses of bovine growth hormone are based on its known biological activity described above. Bovine growth hormone may be administered to young cattle in order to increase their rate of growth and weight gain, thereby decreasing the time required between birth and marketing for beef. The resulting increase in meat production could be significant. Furthermore, bovine growth hormone differs from ovine growth hormone by only a few amino acids. Thus, bovine growth hormone may be administered to sheep to accomplish the same goal in sheep as in cattle, i.e., increasing rate of growth and weight gain and thus increasing meat production. It is also possible that bovine growth hormone can be administered to hogs or other animals to accomplish the same goals.

Basic techniques for cloning DNA sequences are now known. For example, Seeburg, P. H., et al, *Nature*, 270, 486 (19771 describes the cloning of the rat growth hormone gene; Shine, J., et al, *Nature*, 270, 494 (1977) describes the cloning of the human chorionic somatomammotropin gene; and Derynck, R., et al, *Nature*, 285, 542 (1980) describes the cloning of the human fibroblast interferon gene.

Methods for the expression of heterologous DNA in a microorganism are now known. In principle, the heterologous DNA coding sequence is inserted in a DNA transfer vector at a point located within an expressible operon. For the production of a hybrid protein the inserted sequence must be in reading frame phase with the coding sequence of the operon, and oriented in the same direction with respect to translation. When the conditions are met, translation of the operon results in "readthrough" to the inserted coding sequence such that the protein produced is a fusion protein comprising an N-terminal amino acid sequence coded by the expressible operon, followed by an amino acid sequence coded by the insert. See Polisky, B., et al, *Proc.Nat.Acad.Sci.USA*, 73, 3900 (1976); Itakura, K., et al, *Science*, 198, 1056 (1979). Several expressible operons have been employed, including those for β-galactosidase, β-lactamase, and tryptophan.

Abbreviations used herein are those abbreviations commonly accepted and used by one of ordinary skill in the art. For example, these abbreviations are accepted by the *J.Biol. Chem.*, without further elucidation,

SUMMARY OF THE INVENTION

The present invention discloses the cloning of a DNA coding for bovine growth hormone and the expression of the cloned DNA in microorganisms.

mRNA coding for bovine growth hormone is isolated from bovine pituitaries, A reverse transcript (a cDNA copy) of the mRNA is prepared and inserted into a transfer vector, The transfer vector is used to transform bacteria which express the cloned cDNA.

BRIEF DESCRIPTION OF THE DRAWINGS

FIG. 1 is the DNA sequence of the DNA insert in pBP348 encoding bovine pregrowth hormone and the deduced amino acid sequence of the encoded protein.

DETAILED DESCRIPTION OF THE INVENTION

Figure 2:
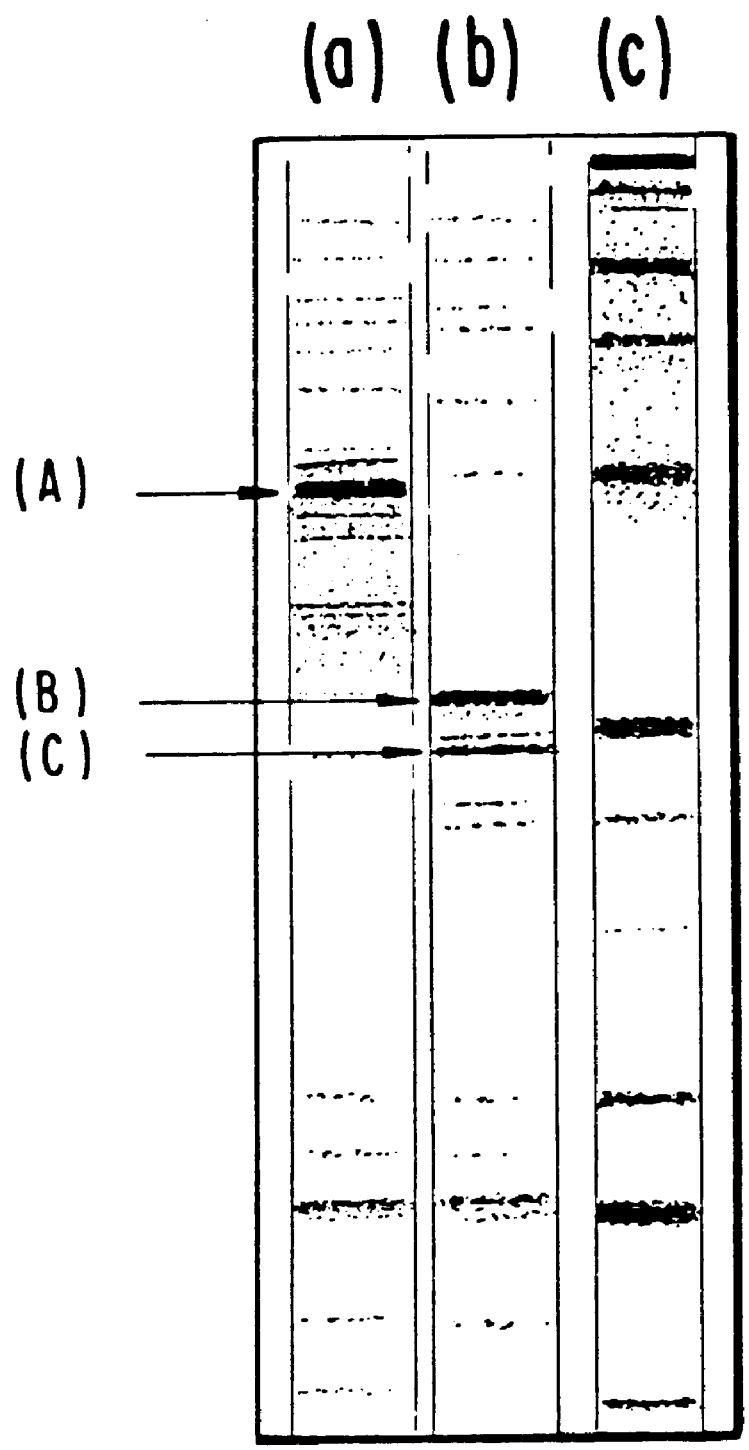
FIG. 2 shows results of gel electrophoresis of extracts from Ecoli transformed with pBP348.

A DNA sequence coding for bovine growth hormone is obtained by using the cDNA method. The basic techniques of the cDNA method are known and can be illustrated by Seeburg, P. H., et al, supra, and Derynck, R., et al, supra. The CDNA is synthesized by using an RNA preparation extracted from bovine pituitaries as the template.

The RNA is isolated from bovine pituitaries using conventional techniques. Polyadenylated RNA is isolated by affinity chromatography. The integrity of the polyadenylated RNA is assessed by performing cell-free translation of the polyadenylated RNA as described by Miller, W. L. and McCarthy, B. J., *J.Biol.Chem.*, 254, 742 (1979) and Martial, J. A., et al, *Proc. Nat.Acad.Sci.USA*, 74, 1816 (1977) and analyzing the proteins produced by SDS-acrylamide gel electrophoresis as described by Laenunli, U.K., *Nature*, 227, 680 (1970). Bovine growth hormone is further identified by an immune precipitation reaction as described by Martial, J. A., et al, *Proc.Nat.Acad.Sci.USA*, supra.

The polyadenylated RNA is used as the template for preparing a double-stranded cDNA copy using conventional techniques. The first cDNA strand is synthesized using reverse transcriptase, an oligo-dT primer and the polyadenylated RNA as described by Miller and McCarthy, supra, and Monahan, J. J., et al, *Biochem.*, 15, 223 (1976). RNA is removed by alkali digestion and the single-stranded cDNA is used to self-prime the synthesis of the second strand by reverse transcriptase, The single-stranded hairpin loop is removed by digestion with S1 nuclease (Leong, J. A., et al, *J.Virol.*, 9, 891 (1972), as described by Ullrich, A., et al *Science* 196: 1313 (1977).

The cDNA is now ready for insertion into an appropriate transfer vector using conventional techniques. For example, a synthetic nucleotide containing a recognition site for a particular restriction endonuclease can be blunt-end ligated to the cDNA, The cDNA and transfer vector are separately incubated with the restriction endonuclease and then annealed to form the transfer vector containing the cDNA. Alternatively, the cDNA can be dC-tailed using dCTP and terminal transferase as described by Roychoudhury, R., et al, *Nucl.Acids Res.*, 3, 863 (1976). The transfer vector, after digestion with a restriction endonuclease such as Pst I can be dG tailed using the same procedure. The dG-tailed transfer vector and dC-tailed cDNA are then annealed to form the transfer vector containing the cDNA. The transfer vector containing the CDNA is then used to transform a suitable host, such as *E. coli* X1776, as described by Cooke, N. E., et al, *J.Biol.Chem.*, 255, 6502 (1980), Colonies are selected for tetracycline resistance. Selected colonies are screened by conventional techniques. These may include (1) removing the cDNA by an appropriate restriction endonuclease and analyzing it by electrophoresis and hybridization (Southern, E. M., *J.Mol. Biol.*, 98, 503 (1975)), or (2) replica-plating as described by Grunstein, M. and Hogness, D. S., *Proc.Nat.Acad.Sci.USA*, 72, 3961 (1975) and hybridizing with an appropriate probe, or (3) examine colonies directly for expression by RIA or other techniques. DNA coding for bovine growth hormone can be prepared from the insert coding for bovine growth pre-hormone. The DNA coding for the pre-hormone is removed by an appropriate restriction endonuclease. For example, if the cDNA is inserted in the Pst I site of the plasmid pBR322, the cDNA insert can be removed by partial digestion with Pst I as the cDNA for bovine GH contains two internal Pst I sites. The cDNA is then digested with Hae II. Alternatively, the recombinant plasmid derived from pBR322 can be digested with Hae II to remove a portion of the cDNA insert, The Hae II digestion removes the DNA coding for the N-terminal signal peptide and two of the three bases coding for the N-terminal Ala of growth hormone. These bases are replaced by serially incubating the insert with the Klenow fragment of DNA polymerase I and the appropriate deoxynucleotide. The cDNA coding for growth hormone is then inserted into an appropriate transfer vector as described above.

The cloned DNA is expressed in bacteria to yield either a fusion protein comprising the bovine growth hormone coded by the inserted sequence, or the bovine growth hormone itself. Several possible techniques are available as options, and may include (a) modification of the coding sequences to provide an exact desired translational starting point; (b) selection or construction of an optimal expression vector; (c) post-translational processing, either by exploiting in vivo processing activity of the host or by in vitro chemical means; and direct expression. When a fusion protein is expressed, modification of the cloned nucleotide sequence will generally be unnecessary as long as the resulting sequence permits translation of the insert in the correct reading frame and no stop codons intervene before the initial codon of the inserted sequence.

Growth pre-hormone or growth hormone is expressed as a fusion protein by insertion of the cDNA into appropriate sites within expressed operons (expression vectors) including for example, the Pst I site in the β-lactamase gene of pBR322 (Villa-Komaroff, L., et al, *Proc.Nat.Acad.Sci.USA*, 75, 3727 (1978)) (Seeburg, P., et al *Nature* 274: 795 (1978)) the EcoRI site of pBR322 carrying the lac control region and coding sequence for β-galactosidase (Itakura, K., supra), or the HindIII site of the trpD gene of plasmid ptrpED50 Martial, J., et al, *Science*, 205, 602 (1979)). Modifications of sequence length by one or two nucleotides in order to achieve correct reading frame phase are well known in the art. Insertions at the Pst I site of pBR322, with the aid of the tailing procedure, occur in correct phase and reading frame with a probability of 1/6.

Growth pre-hormone or growth hormone is prepared from a fusion protein susceptible of specific cleavage in vitro. The cloned nucleotide sequence is modified to code for amino acid sequences providing specificity for a proteolytic enzyme. A useful sequence is AspAspAspAspLys, cleaved preferentially by the enzyme enterokinase, as described in copending application Ser. No. 125,878, filed Feb. 29, 1980, incorporated herein by reference. As described therein, a linking nucleotide sequence coding for the foregoing amino acid sequence is inserted adjacent the nucleotide sequence coding for the amino terminus of growth pre-hormone.

For growth pre-hormone such insertion requires modification of the original CDNA insert, by removal of nucleotides on the 5' end of the growth pre-hormone coding sequence. The d cDNA insert for growth hormone, described supra, does not need to be modified. The modification of the insert for growth pre-hormone is accomplished either by controlled digestion of the 3' end of the insert using 3' exonuclease or T4 DNA polymerase or by the combination of restriction endonuclease cleavage at a point to the 5' side of the desired starting point and chemical synthesis to restore that portion of the desired sequence thus removed. For further details of these procedures, see copending application Ser. No. 125,878, By following these procedures, preferably using T4 DNA polymerase and S1 nuclease, the cDNA sequence coding for growth pre-hormone and lacking the 5' untranslated region is obtained. The linker nucleotide sequence coding for the foregoing amino acid sequence is blunt-end ligated to the cDNA coding for either growth pre-hormone or growth hormone using DNA ligase as described by Valenzuela et al, *Nature*, 280, 815 (1979). The modified CDNA sequence is inserted into a fusion protein express vector as previously described. Host bacteria, such as *E. coli* HB101, RR1, or X1776, or other bacteria are transformed by the recombinant vectors bearing the inserted growth pre-hormone coding region. Transformants are selected for resistance to ampicillin. Transformants are then grown under conditions suitable for expression of the fusion protein. After expression of the fusion protein, the growth pre-hormone or growth hormone is cleaved out by enzymatic hydrolysis using enterokinase.

By the use of appropriate expression transfer vectors, the growth pre-hormone of the present invention is expressed directly, i.e., not fused to any procaryotic protein. The underlying principle of direct expression is that the inserted DNA segment entirely replaces the coding segment normally transcribed and translated by the bacterial control region. The essential component of the control region to be preserved is termed the expression unit, which includes a promoter and a ribosomal binding site capable of acting in the host organism. It is not necessary to remove all of the nucleotides coding for the host portion of the fusion protein. The relationship between the ribosomal binding site and the start codon (AUG) is such that the start codon may be located anywhere within 3–11 nucleotides of the ribosomal binding site. Shine, J., et al, *Proc.Nat.Acad.Sci.USA*, 71, 1342 (1974) and Steitz, J., *Proc.Nat.Acad.Sci.USA*, 72, 4734 (1975), In this 3–11 nucleotide region, the first AUG to be encountered sets the reading frame for translation. In the case of ptrpE30, derived from ptrpED50 described, supra, and containing the operator, promoter, attenuator and ribosome binding sequences of the tryptophan operon together with the nucleotide sequence coding for seven amino acids of the trp E portein followed by a HindIII site, the removal of a minimum of 23–29 nucleotides from the HindIII site provides a site for insertion of the cDNA insert under tryptophan operon control.

For the direct expression of growth pre-hormone, the 3original cDNA insert is modified as described above to remove the 5' untranslated region. A vector for direct expression can be constructed by modification of ptrpE30 by removing 23–29 nucleotides using T4 DNA polymerase and S1 nuclease as described above. A linker nucleotide sequence containing the restriction sequence for Bam HI endonuclease is blunt-end ligated to both the modified cDNA insert and the modified ptrpE30 by the procedure of Valenzuela, et al, supra. This is done to facilitate insertion which is performed essentially as described by Ullrich, A. et al, *Science*, 196, 1313 (1977). Host bacteria such as *E. coli*, HB101, RR1, or X1776 or other bacteria are transformed vectors bearing the inserted growth pre-hormone coding region. Transformants are selected for resistance to ampicillin and then grown under conditions suitable for expression of growth pre-hormone.

Growth hormone can be expressed directly by following the procedure described in Goeddel, D. V., et al, *Nature*, 281, 544 (1979). Alternatively, a linker nucleotide sequence containing the Bam HI site and the start codon (AUG) can be blunt-end ligated to the cDNA coding for growth hormone. This modified cDNA is then inserted into the modified ptrpE30 as described above.

Growth pre-hormone is converted to growth hormone by removal of the N-terminal sequence of hydrophobic amino acids that comprise the signal peptide. In vitro removal of the signal peptide might be carried out by treating the protein extracted from transformed, induced cells with a preparation of "rough" microsomes as described by Jackson, R. C. and Blobel, G., *Proc. Nat.Acad.Sci.USA*, 74, 5598 (1977). In vivo removal of the signal peptide may occur during direct bacterial expression of the growth pre-hormone coding sequence. Bacterial and mammalian signal peptides share sequence similarities. Proteins having mammalian signal peptides may be processed by bacterial cells resulting in excretion of growth hormone into the periplasmic space or into the medium.

Growth pre-hormone and growth hormone synthesized as described are purified by techniques well known in the art, including for example, gel filtration, ion exchange chromatography, affinity chromatography and differential solubility techniques.

The details of the present invention will be further described by the following examples, In these examples, digestions with restriction endonucleases were carried out under conditions optimized for each enzyme. Restriction endonucleases, their nomenclature and site specificity have been described in detail by Roberts, R., *Crit.Rev.Biochem.*, 4, 123 (1976). Enzymes were obtained commercially (New England Biolabs, Cambridge, Mass.) and optimal conditions according to supplier's recommendations were employed unless noted otherwise. Reverse transcriptase was provided by Dr. J. Beard, Life Sciences, Inc., St. Petersburg, Fla. The use of reverse transcriptase and suitable reaction conditions have been described previously by Seeburg, P. H., et al, *Nature* 276, 795 (1978); Seeburg, P. H., et al, supra; and Shine, J., et al, supra., T4 DNA polymerase was obtained from New England Biolabs. The use of T4 DNA polymerase and suitable reaction conditions have been previously described in copending application Ser. No. 125,878. Micrococcal S1 nuclease was obtained from Miles Laboratories, Elkhart, Ind. The use of S1 nuclease and suitable reaction conditions have been previously described by Ullrich, A., supra. Terminal deoxynucleotide transferase was obtained from Enzo Biochemicals, New York, N.Y. The use of this enzyme and suitable reaction conditions have been previously described by Roychoudhury et al, supra. The Klenow fragment of DNA polymerase I was obtained from Boehringer Biochemicals, Indianapolis, Ind.

EXAMPLE 1

Synthesis of bovine growth pre-hormone cDNA. Female bovine pituitaries were collected shortly after killing and were frozen immediately in liquid nitrogen. Total RNA was prepared by homogenizing the pituitaries in a guanidine thiocyanate solution, Chirgwin, J. M., et al, *Biochem.*, 18, 5294 (1979). The RNA was centrifuged through 5.7M CsCl as described by Ullrich, A.,. et al, supra, The RNA was then extracted with phenol and precipitated with ethanol. Polyadenylated RNA was purified using oligo-dT-cellulose affinity chromatography as described by tiller and McCarthy, supra, and Aviv, H. and Leder, P., *Proc.Nat.Acad.Sci.USA*, 69, 1408 (1972), The polyadenylated RNA was translated in a cell-free system using rabbit reticulocytes as described by Miller and McCarthy, supra, and Martial, J. A., et al, supra, (1977). Bovine growth pre-hormone synthesized in this sytem was immune;precipitated using a heterologous anti-ovine growth hormone antiserum and prepared by adsorption to formalin-fixed *Staphylococcus aureus* Cowan strain I as described by Martial, J. A., et al, supra, (1977) The $^{35}$S-proteins were electrophoresed on 12.5% SDS slab polyacrylamide gels as described by Laemmli, supra. This analysis indicated that polyadenylated RNA coding for bovine growth pre-hormone represented about 12.6% of the total pituitary polyadenylated RNA.

Polyadenylated RNA was reverse-transcribed into single-stranded cDNA using reverse transcriptase by the procedure described by Miller and McCarthy, supra, and Monahan et al, supra. RNA was removed by alkaline hydrolysis. The single-stranded cDNA was extracted with phenol, chromatographed over G-50 Sephadex (trademark Pharmacia, Inc., Uppsala, Sweden) and ethanol precipitated, The single-stranded cDNA was used to self-prime the synthesis of the second strand of cDNA using reverse transcriptase as described above. The single-stranded at "hairpin loop" at the 3' end of the first strand of cDNA was removed by digestion with S1 nuclease as described by Leong et al, supra and Ullrich, A. et al, supra. The double-stranded cDNA was purified by phenol extraction, chromatography over G-50 Sephadex and ethanol precipitation, The double-stranded cDNA was 3'dCMP tailed using dCTP and terminal transferase as described by Roychoudhury et al, supra.

Plasmid pBR322 was cleaved by Pst I endonuclease and tailed with dGMP by the previously described tailing procedure except that dGTP is used instead of dCTP. 50 ng of the dG-tailed, Pst I cleaved plasmid pBR322 and 20 ng of the dC-tailed double-stranded CDNA were annealed in a 50 μl reaction as described by Cooke, et al, supra.

Transformation of *E. coli* X1776 with the plasmid preparation was carried out as follows. *E. coli* X1776 were rendered permeable to DNA by incubation in 75 mM CaCl$_2$, 5 mM MgCl$_2$, 10 mM Tris, pH 7.5, for 20 minutes at 4° C. Plasmid and bacteria were incubated for 60 minutes at 4° C., and then 2 minutes at 41° C. Transformed colonies were selected for tetracycline resistance. The presence of cloned DNA was determined by colony hybridization to freshly prepared bovine pituitary $^{32}$P labelled cDNA as described by Grunstein and Hogness, supra. Plasmid DNA was prepared from selected colonies, cut with Pst I, electrophoresed on 1% agarose, stained with ethidium bromide and photographed and finally transferred to nitrocellulose filters by the method of Southern, supra. The presence of growth hormone sequences in the transferred DNA was assessed by hybridization to cloned full length rat hormone cDNA (Seeburg, P. H., et al, supra), labelled by nick translation (Maniatis, R., et al, *Proc.Nat.Acad.Sci.USA*, 72, 1184 (1975)). One clone was obtained which hybridized with the nick-translated DNA and was designated pBP348. The insert contains 831 base pairs.

EXAMPLE 2

Sequence analysis of the cDNA. Plasmid pBP348 was cut with Pst I and the phosphate on the 5' ends of the DNA fragments was removed with alkaline phosphatase and replaced with [$^{32}$P] phosphate using polynucleotide kinase. Subsequent cutting with a variety of other restriction endonucleases, polyacrylamide gel electrophoresis, and staining and autoradiography of the bands of DNA provide a restriction map of the cloned DNA. A large batch of pBP348 was then prepared and cut with Pst I, Pvu II or Sau 3A, labeled with gamma [$^{32}$P]ATP and polynucleotide kinase, and then cut with other enzymes to yield DNA fragments labeled at a single end. These fragments were prepared by elution from polyacrylamide gel and sequenced as described by Cooke et al, supra, and Maxam, A. M. and Gilbert, W., *Proc.Nat. Acad. Sci.USA*, 74, 1560 (1977). The sequence for the inserted cDNA is shown in FIG. 1 together with the corresponding predicted amino acid sequence coded by the sense strand, i.e., the strand corresponding in sequence to the respective mRNA.

The correct reading frame is recognized by the lack of termination codons over a substantial portion of the inserts. The amino acid positions are numbered beginning with the amino-terminal amino acid of bovine growth hormone and proceeding in the positive direction to the carboxy terminal end and in the negative direction to the first AUG codon presumed to be the point of translation initiation. The sequences suggest, in common with many other hormones, the synthesis of growth hormone involves posttranslational processing. The translation of growth hormone mRNA yields a precursor, growth pre-hormone, containing a signal peptide which may be released during the transit into the endoplasmic reticulum.

EXAMPLE 3

Synthesis of cDNA coding for bovine growth hormone. Plasmid pBP348 is digested with Hae II endonuclease generating a 1600 base pair fragment. One Hae II site is within the cDNA insert coding for growth pre-hormone and the second site is within the pBR322 portion of the plasmid. The digestion yields the following:

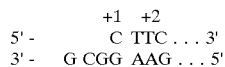

Bovine GH may begin with either the +1 ala or the +2 phe residue at the NH$_2$ terminal end (Dayhoff et al, supra), thus one might attempt to complete the ala codon or one might attempt to delete it. This deletion approach is accomplished by incubating the DNA with dATP and the Klenow fragment of DNA polymerase I, as the first base of the +2 phe codon (on the 3'–5' strand) is A. This reaction yields the following:

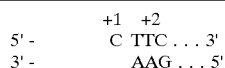

The DNA is extracted with phenol and precipitated. Excess dATP and the digested bases are removed by chromatography on G-50 Sephadex. The remaining 5' protuding C of the +1 ala codon is then removed with S$_1$ nuclease as described by Shine et al Nature 285:456 (1980). This digestion yields:

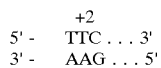

This DNA can be inserted into a transfer vector as described in Example 1.

EXAMPLE 4

Expression of bovine growth hormone. Bovine growth hormone can be expressed by any of the methods described above. For purposes of illustration only, production of human growth hormone by direct expression will be described. It is understood that bovine growth hormone can be prepared in the same manner and that bovine or human growth hormone can be prepared by any of the other described methods.

(A) Expression of bovine growth pre-hormone as a fusion protein was demonstrated by performing a radioimmunoassay experiment and performing a minicell experiment. In the radioimmunoassay experiment, *E. coli* X1776 containing pBR348 or *E. coli* containing pBR322 as the control were grown in nutrient broth and collected by centrifugation. The cells were resuspended and lysed and radiolabelled ovine growth hormone and antibody ovine (or bovine) to growth hormone were added. The immune complex was precipitated and radioactivity measured. This experiment shows that the fusion protein retains some bovine growth hormone immunoactivity, To further illustrate the production of a fusion protein, a minicell experiment was performed by following the procedure described by Meagher, R. B., et al, *Cell*, 10, 521 (1977). FIG. 2 shows the gel electrophoresis bands resulting from *E. coli* X1776 minicells. Band (a) was obtained from X1776 transformed with pBP348. Band (b) was obtained from X1776 transformed with pBR322. Band (c) is molecular weight markers. (A) indicates the fusion product of β-lactamase and bovine growth pre-hormone, (B) indicates pre-lactamase and (C) indicates β-lactamase. This experiment shows that pBP348 makes a fusion protein consisting of 183 amino acids of β-lactamase, 217 amino acids of bovine growth pre-hormone and a few linking amino acids coded by the normally untranslated 5' region. The total molecular weight seen, approximately 45,000, agrees with the predicted molecular weight of the hybrid protein.

(B) For the direct expression of bovine growth pre-hormone the insert DNA is first separated from pBP348 by partial Pst I endonuclease digestion and purified by preparative gel electrophoresis. A 15 μg sample of purified insert DNA is then modified by suspending the DNA in water to which is added a concentrated solution of salts such that the final composition comprises 70 mM Tris, pH 8.8, 70 mM MgCl$_2$, 10 mM dithiothreitol and 13.75 units of T4 DNA polymerase in a total volume of 250 μl. The reaction mixture is incubated at 37° C. for several minutes and then dATP is added to a concentration of 50 mM to terminate endonucleolytic digestion at the next adenine residue. After 30 seconds of additional incubation, the enzyme is inactivated by heat treatment at 65° C. for five minutes. This process is repeated twice more, once in which dCTP is used in place of dATP and finally in which dTTP is again used. The treated DNA is recovered by ethanol precipitation. Digestion with S1 nuclease to provide blunt ends is carried out as described by Ullrich, A., et al, supra. This procedure is designed to produce a DNA molecule terminated at the start codon at the position number −26. Such molecules will be translated when inserted in an expression vector having an insertion site about 3–11 nucleotides from the ribosome binding site sequence of an expression unit.

A vector for direct expression is constructed by modification of the plasmid ptrpE30 by the removal of 23–29 nucleotides using T4 DNA polymerase and S1 nuclease as described above.

The modified cDNA and the modified expression vector are provided with a specific linker having the sequence 5'-CCGGATCCGG-3' on one strand and its complementary sequence on the other by blunt-end ligation using DNA ligase as described by Valenzuela, supra. The linkers provide restriction sites sensitive to Bam HI endonuclease which are employed to facilitate insertion. Insertion is accomplished by following the procedure of Ullrich, A., et al, supra. Host bacteria E. coli HB101 or E. coli X1776 are transformed by the recombinant vectors bearing the inserted modified growth pre-hormone coding region and transformants are selected for resistance to ampicillin. A single transformant designated ptrpE30/bGH is selected for further analysis.

Bacterial cells transformed by ptrE30/bGH are grown in a standard minimal medium (M9) supplemented with Leu, Pro, vitamin B1 and ampicillin at 37° C. In early log phase, the trp operon is induced by the addition of β-indolylacrylic acid (30 μg/ml medium). Control cultures are left uninduced. After three more hours of growth, 1,5 ml of cells are radioactively labelled by the addition of 20 μCi of $^{35}$S-L-Met and incubated for 10 minutes. The cells are collected by centrifugation, washed and resuspended in 250 μl of buffer containing 10% (v/v) glycol, 5% (v/v) 8-mercaptoethanol and 2.3% (w/v) SDS in 0.0625M Tris, pH 6.8, The suspension is boiled for five minutes, then applied to a 10% (w/v) SDS-polyacrylamide gel and fractionated by electrophoresis. The protein bands are visualized by autoradiography, The results show the existence of a new protein band of about 24,000 daltons not observed in the un-induced or non-transformed cultures.

The bovine growth pre-hormone is purified by conventional techniques including, for example, gel filtration, ion exchange chromatography, affinity chromatography and differential solubility techniques. Growth pre-hormone is converted to growth hormone by following the procedure described by Jackson, et al, supra.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

Plasmid pBP348, containing bovine growth hormone encoding sequences, and transfected into E. coli strain X1776, has been deposited at the American Type Culture Collection, Rockville, Md., on Aug. 26, 1980, and has ATCC No. 31686.

What is claimed is:

1. A composition of DNA molecules which consists of DNA molecules encoding bovine growth hormone comprising the amino acid sequence:

```
                                        10
phe pro ala met ser leu ser gly leu phe ala asn
                            20
ala val leu arg ala gln his leu his gln leu ala
                    30
ala asp thr phe lys glu phe glu arg thr tyr ile
            40
pro glu gly gln arg tyr ser ile gln asn thr gln
 50                                             60
val ala phe cys phe ser glu thr ile pro ala pro
                                    70
thr gly lys asn glu ala gln gln lys ser asp leu
                            80
glu leu leu arg ile ser leu leu leu ile gln ser
                    90
trp leu gly pro leu gln phe leu ser arg val phe
            100
thr asn ser leu val phe gly thr ser asp arg val
110                                             120
tyr glu lys leu lys asp leu glu glu gly ile leu
                                    130
ala leu met arg glu leu glu asp gly thr pro arg
                            140
ala gly gln ile leu lys gln thr tyr asp lys phe
                    150
asp thr asn met arg ser asp asp ala leu leu lys
            160
asn tyr gly leu leu ser cys phe arg lys asp leu
170                                             180
his lys thr glu thr tyr leu arg val met lys cys
                                190 191
arg arg phe gly glu ala ser cys ala phe.
```

2. A recombinant DNA molecule which comprises a segment encoding a protein in a condition substantially free of DNA encoding bovine pituitary protein other than bovine growth hormone, wherein said segment encodes a protein comprising the amino acid sequence:

```
                                        10
phe pro ala met ser leu ser gly leu phe ala asn ala val leu
                20                                          30
arg ala gln his leu his gln leu ala ala asp thr phe lys glu
                                    40
phe glu arg thr tyr ile pro glu gly gln arg tyr ser ile gln
                50                                          60
```

```
                                        -continued
asn thr gln val ala phe cys phe ser glu thr ile pro ala pro
                                 70
thr gly lys asn glu ala gln gln lys ser asp leu glu leu leu
                 80                                  90
arg ile ser leu leu leu ile gln ser trp leu gly pro leu gln
                            100
phe leu ser arg val phe thr asn ser leu val phe gly thr ser
                110                              120
asp arg val tyr glu lys leu lys asp leu glu glu gly ile leu
                            130
ala leu met arg glu leu glu asp gly thr pro arg ala gly gln
                140                              150
ile leu lys gln thr tyr asp lys phe asp thr asn met arg ser
                            160
asp asp ala leu leu lys asn tyr gly leu leu ser cys phe arg
                170                              180
lys asp leu his lys thr glu thr tyr leu arg val met lys cys
                            190 191
arg arg phe gly glu ala ser cys ala phe.
```

3. The recombinant DNA molecule of claim 2 wherein said segment comprises the nucleotide sequence:

```
                          10
TTC CCA GCC ATG TCC TTG TCC GGC CTG TTT GCC AAC GCT GTG CTC
             20                              30
CGG GCT CAG CAC CTG CAC CAG CTG GCT GCT GAC ACC TTC AAA GAG
                          40
TTT GAG CGT ACC TAC ATC CCG GAG GGA CAG AGA TAC TCC ATC CAG
             50                              60
AAC ACC CAG GTT GCC TTC TGC TTC TCC GAA ACC ATC CCG GCC CCC
                          70
ACG GGC AAG AAT GAG GCC CAG CAG AAA TCA GAC TTG GAG CTG CTT
             80                              90
CGC ATC TCA CTG CTC CTC ATC CAG TCG TGG CTT GGG CCC CTG CAG
                         100
TTT CTC AGC AGA GTC TTC ACC AAC AGC TTG GTG TTT GGC ACC TCG
            110                             120
GAC CGT GTC TAT GAG AAG CTG AAG GAC CTG GAG GAA GGC ATC TTG
                         130
GCC CTG CTG CGG GAG CTG GAA GAT GGC ACC CCC CGG GCT GGG CAG
            140                             150
ATC CTC AAG CAG ACC TAT GAC AAA TTT GAC ACA AAC ATG CGC AGT
                         160
GAC GAC GCG CTG CTC AAG AAC TAC GGT CTG CTC TCC TGC TTC CGG
            170                             180
AAG GAC CTG CAT AAG ACG GAG ACG TAC CTG AGG GTC ATG AAG TGC
                         190 191
CGC CGC TTC GGG GAG GCC AGC TGT GCC TTC.
```

4. A microorganism transformed with the DNA molecule of claim 3.

5. The recombinant DNA molecule of claim 2 which further comprises sequences capable of effecting the expression of said segment when contained in a microorganism.

6. A microorganism transformed with the DNA molecule of claim 5.

7. A method to produce bovine growth hormone which method comprises culturing the microorganism of claim 6 under conditions wherein said expression is effected to produce said bovine growth hormone; and recovering the bovine growth hormone from the culture.

8. A microorganism transformed with the DNA molecule of claim 2.

9. A microorganism that contains bovine growth hormone which hormone has the amino acid sequence:

```
                                  10
phe pro ala met ser leu ser gly leu phe ala asn ala val leu
                  20                                  30
arg ala gln his leu his gln leu ala ala asp thr phe lys glu
                                  40
phe glu arg thr tyr ile pro glu gly gln arg tyr ser ile gln
                  50                                  60
asn thr gln val ala phe cys phe ser glu thr ile pro ala pro
                                  70
thr gly lys asn glu ala gln gln lys ser asp leu glu leu leu
                  80                                  90
arg ile ser leu leu leu ile gln ser trp leu gly pro leu gln
                                  100
phe leu ser arg val phe thr asn ser leu val phe gly thr ser
                  110                                 120
asp arg val tyr glu lys leu lys asp leu glu glu gly ile leu
                                  130
ala leu met arg glu leu glu asp gly thr pro arg ala gly gln
                  140                                 150
ile leu lys gln thr tyr asp lys phe asp thr asn met arg ser
                                  160
asp asp ala leu leu lys asn tyr gly leu leu ser cys phe arg
                  170                                 180
lys asp leu his lys thr glu thr tyr leu arg val met lys cys
                                  190 191
arg arg phe gly glu ala ser cys ala phe.
```

10. A method to produce bovine growth hormone which method comprises recovering the bovine growth hormone from the microorganism of claim 9.

11. A method to produce bovine growth hormone from a recombinant DNA vector, which method comprises:

a) preparing cDNA from RNA isolated from a bovine source which DNA encodes bovine growth hormone;

b) preparing a first DNA segment from the cDNA prepared in step a);

c) preparing a second DNA segment from a host vector capable of replicating in a microorganism and containing control sequences for expression;

d) ligating the first DNA segment to the second DNA segment to form an expression vector effective in expressing the first DNA segment encoding bovine growth hormone;

e) inserting the expression vector into a microorganism;

f) growing the microorganism in culture under conditions wherein said bovine growth hormone is produced; and g) recovering said bovine growth hormone from the culture.

12. A composition of DNA molecules which consists of DNA molecules encoding bovine pregrowth hormone of the amino acid sequence:

```
-26                     -20
met met ala ala gly pro arg thr ser leu leu leu ala phe ala -10                                         1
leu leu cys leu pro trp thr gln val val gly ala phe pro ala 10
met ser leu ser gly leu phe ala asn ala val leu arg ala gln 20                                     30
his leu his gln leu ala ala asp thr phe lys glu phe glu arg 40
thr tyr ile pro glu gly gln arg tyr ser ile gln asn thr gln 50                                         60
val ala phe cys phe ser glu thr ile pro ala pro thr gly lys 70
asn glu ala gln gln lys ser asp leu glu leu leu arg ile ser 80                                     90
leu leu leu ile gln ser trp leu gly pro leu gln phe leu ser 100
arg val phe thr asn ser leu val phe gly thr ser asp arg val 110                             120
tyr glu lys leu lys asp leu glu glu gly ile leu ala leu met 130
arg glu leu glu asp gly thr pro arg ala gly gln ile leu lys 140                                 150
gln thr tyr asp lys phe asp thr asn met arg ser asp asp ala 160
leu leu lys asn tyr gly leu leu ser cys phe arg lys asp leu 170                             180
his lys thr glu thr tyr leu arg val met lys cys arg arg phe 190 191
gly glu ala ser cys ala phe.
```

13. A recombinant DNA molecule which comprises a segment encoding a protein in a condition substantially free of DNA encoding bovine pituitary protein other than bovine pregrowth hormone, wherein said segment encodes a protein of the amino acid sequence:

```
                                    -26                     -20
                                    met met ala ala gly pro arg thr ser leu leu leu ala phe ala -10                                         1
                                    leu leu cys leu pro trp thr gln val val gly ala phe pro ala 10
                                    met ser leu ser gly leu phe ala asn ala val leu arg ala gln 20                                     30
                                    his leu his gln leu ala ala asp thr phe lys glu phe glu arg 40
                                    thr tyr ile pro glu gly gln arg tyr ser ile gln asn thr gln 50                                         60
                                    val ala phe cys phe ser glu thr ile pro ala pro thr gly lys 70
                                    asn glu ala gln gln lys ser asp leu glu leu leu arg ile ser 80                                     90
                                    leu leu leu ile gln ser trp leu gly pro leu gln phe leu ser 100
                                    arg val phe thr asn ser leu val phe gly thr ser asp arg val
```

```
                                    110                                    120
                        tyr glu lys leu lys asp leu glu glu gli ile leu ala leu met
                                                130
                        arg glu leu glu asp gly thr pro arg ala gly gln ile leu lys
                        140                                    150
                        gln thr tyr asp lys phe asp thr asn met arg ser asp asp ala
                                                160
                        leu leu lys asn tyr gly leu leu ser cys phe arg lys asp leu
                        170                                    180
                        his lys thr glu thr tyr leu arg val met lys cys arg arg phe
                                                190 191
                        gly glu ala ser cys ala phe.
```

14. The recombinant DNA molecule of claim 13 wherein said segment has the nucleotide sequence:

```
        -26                            -20
        ATG ATG GCT GCA GGC CCC CGG ACC TCC CTG CTC CTG GCT TTC GCC CTG
        -10                                                  1
        CTC TGC CTG CCC TGG ACT CAG GTG GTG GGC GCC TTC CCA GCC ATG TCC
                          10                                        20
        TTG TCC GGC CTG TTT GCC AAC GCT GTG CTC CGG GCT CAG CAC CTG CAC
                                    30
        CAG CTG GCT GCT GAC ACC TTC AAA GAG TTT GAG CGT ACC TAC ATC CCG
              40                                  50
        GAG GGA CAG AGA TAC TCC ATC CAG AAC ACC CAG GTT GCC TTC TGC TTC
                              60                                          70
        TCC GAA ACC ATC CCG GCC CCC ACG GGC AAG AAT GAG GCC CAG CAG AAA
                                          80
        TCA GAC TTG GAG CTG CTT CGC ATC TCA CTG CTC CTC ATC CAG TCG TGG
                        90                              100
        CTT GGG CCC CTG CAG TTT CTC AGC AGA GTC TTC ACC AAC AGC TTG GTG
                                    110
        TTT GGC ACC TCG GAC CGT GTC TAT GAG AAG CTG AAG GAC CTG GAG GAA
              120                              130
        GGC ATC TTG GCC CTG ATG CGG GAG CTG GAA GAT GGC ACC CCC CGG GCT
                                140                                    150
        GGG CAG ATC CTC AAG CAG ACC TAT GAC AAA TTT GAC ACA AAC ATG CGC
                                    160
        AGT GAC GAC GCG CTG CTC AAG AAC TAC GGT CTG CTC TCC TGC TTC CGG
                        170                              180
        AAG GAC CTG CAT AAG ACG GAG ACG TAC CTG AGG GTC ATG AAG TGC CGC
                                    190 191
        CGC TTC GGG GAG GCC AGC TGT GCC TTC.
```

15. A microorganism transformed with the DNA molecule of claim 14.

16. The recombinant DNA molecule of claim 13 which further comprises sequences capable of effecting the expression of said segment when contained in a microorganism.

17. A microorganism transformed with the DNA molecule of claim 16.

18. A method to effect expression of the segment of the DNA molecule of claim 16 which method comprises culturing a microorganism containing said DNA molecule under conditions wherein said expression is effected.

19. A microorganism transformed with the DNA molecule of claim 13.

20. A microorganism that contains bovine pregrowth hormone which pregrowth hormone has the amino acid sequence:

```
-26                    -20
met met ala ala gly pro arg thr ser leu leu leu ala phe ala -10                               1
leu leu cys leu pro trp thr gln val val gly ala phe pro ala 10
met ser leu ser gly leu phe ala asn ala val leu arg ala gln 20                          30
his leu his gln leu ala ala asp thr phe lys glu phe glu arg 40
thr tyr ile pro glu gly gln arg tyr ser ile gln asn thr gln 50                                  60
val ala phe cys phe ser glu thr ile pro ala pro thr gly lys 70
asn glu ala gln gln lys ser asp leu glu leu leu arg ile ser 80                                  90
leu leu leu ile gln ser trp leu gly pro leu gln phe leu ser 100
arg val phe thr asn ser leu val phe gly thr ser asp arg val 110                         120
tyr glu lys leu lys asp leu glu glu gly ile leu ala leu met 130
arg glu leu glu asp gly thr pro arg ala gly gln ile leu lys 140                                 150
gln thr tyr asp lys phe asp thr asn met arg ser asp asp ala 160
leu leu lys asn tyr gly leu leu ser cys phe arg lys asp leu 170                                 180
his lys thr glu thr tyr leu arg val met lys cys arg arg phe 190 191
gly glu ala ser cys ala phe.
```

21. A method to produce bovine growth hormone from a recombinant DNA vector, which method comprises:
   a) preparing cDNA from RNA isolated from a bovine source which DNA encodes bovine pregrowth hormone;
   b) preparing a first DNA segment from the cDNA prepared in step a);
   c) preparing a second DNA segment from a host vector capable of replicating in a microorganism and containing control sequences for expression;
   d) ligating the first DNA segment to the second DNA segment to form an expression vector effective in expressing the first DNA segment encoding bovine pregrowth hormone;
   e) inserting the expression vector into a microorganism; and
   f) growing the microorganism in culture under conditions wherein said bovine pregrowth hormone is produced.

* * * * *

UNITED STATES PATENT AND TRADEMARK OFFICE
CERTIFICATE OF CORRECTION

PATENT NO. : 6,692,941 B1 Page 1 of 1
DATED : February 17, 2004
INVENTOR(S) : Walter L. Miller et al.

It is certified that error appears in the above-identified patent and that said Letters Patent is hereby corrected as shown below:

<u>Title page,</u>
After Item [73], Assignee, insert the following paragraph:

-- This invention was made with Government support under Grant No. AM00422 and GM25549, awarded by the National Institutes of Health. The Government has certain rights in this invention. --

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,692,941 B1
DATED         : February 17, 2004
INVENTOR(S)   : Miller et al.

It is certified that error appears in the above-identified patent and that said Letters Patent is hereby corrected as shown below:

Title page,
Item [*] Notice, delete "Subject to any disclaimer, the term of this patent is extended or adjusted under 35 U.S.C. 154(b) by 1,826 days.".

Signed and Sealed this

Twentieth Day of September, 2005

JON W. DUDAS
*Director of the United States Patent and Trademark Office*